United States Patent [19]

Sharma et al.

[11] Patent Number: 5,225,198
[45] Date of Patent: Jul. 6, 1993

[54] TRANSDERMAL ADMINISTRATION OF SHORT OR INTERMEDIATE HALF-LIFE BENZODIAZEPINES

[75] Inventors: Kuldeepak Sharma, Mountain View; Darth M. Dunbar, San Mateo, both of Calif.

[73] Assignee: Cygnus Therapeutic Systems, Redwood City, Calif.

[21] Appl. No.: 750,571

[22] Filed: Aug. 27, 1991

[51] Int. Cl.⁵ ............................................. A61F 13/00
[52] U.S. Cl. .................................. 424/443; 424/447; 424/448; 424/449
[58] Field of Search ................ 424/449, 448, 447, 443

[56] References Cited

U.S. PATENT DOCUMENTS

| | | | |
|---|---|---|---|
| 3,987,052 | 10/1976 | Hester, Jr. | 424/443 |
| 4,557,934 | 12/1985 | Cooper | 424/449 |
| 4,973,468 | 11/1990 | Chiang et al. | 424/449 |

FOREIGN PATENT DOCUMENTS 61-254519 7/1985 Japan.
61-33129 2/1986 Japan.

OTHER PUBLICATIONS

USP Drug Information for the Health Care Professional, 10th Edition, (1990) pp. 595–602.
Abernethy et al., *J. Clin. Psychiatry* (1983) 44(8, Sect. 2):3 pages total.
Smith et al., *Psychopharmacology* (1984) 84:452–456.
Shell et al., *Cardiology* (1986) 4(4):697–704.
Stahl et al., *Psychopharmacology Bulletin* (1985) 21(3):657–662.
Cho et al., *J. Pharmaceutical Sciences* (1983) 72(4):356–362.
Ormerod et al., *British J. Dermatology* (1989) 121:411–415.
Adams et al., *Anal. Chem.* (1984) 56(9):1590–1594.
Yalkowsky et al., *J. Pharmaceutical Sciences* (1983) 72(9):1014–1017.

*Primary Examiner*—Thurman K. Page
*Assistant Examiner*—Leon R. Horne
*Attorney, Agent, or Firm*—Morrison & Foerster

[57] ABSTRACT

Method and laminated composite for administering short or intermediate half-life benzodiazepines such as alprazolamine or triazolam transdermally to treat conditions such as anxiety in the case of alprazolam and insomnia in the case of triazolam. The composite comprises an impermeable backing layer and a reservoir layer containing the benzodiazepine and a permeation enhancer combined with a solvent-based acrylic polymer adhesive with the amounts of benzodiazepine and enhancer being sufficient to cause the benzodiazepine to pass through the skin at a rate in excess of about one $\mu g/cm^2/hr$.

10 Claims, 1 Drawing Sheet

TRANSDERMAL ADMINISTRATION OF SHORT OR INTERMEDIATE HALF-LIFE BENZODIAZEPINES

DESCRIPTION

1. Technical Field

This invention relates to methods and devices for administering short- and intermediate-acting benzodiazepines, particularly alprazolam and triazolam, transdermally.

2. Background

Alprazolam (8-chloro-1-methyl-6-phenyl-4H-1,2,4-triazolo(4,3-a) (1,4)benzodiazepine) is a short to intermediate half-life benzodiazepine drug. It is sold commercially in the U.S. under the brand name Xanax in the form of tablets for treatment of anxiety, depression, and panic disorders. U.S. Pat. No. 3,987,052 describes the preparation and oral administration of alprazolam. It is given orally in doses of 0.25 to 0.5 mg with a maximum dose up to 4 mg for adults. Therapeutic plasma concentrations are typically in the 17 to 30 ng/ml range. (*USP Drug Information for the Health Care Professional*, page 595, 10th Ed., 1990.) The pharmacokinetics and pharmacodynamics of alprazolam after oral and intravenous administration are reported in *J. Clin. Psychiatry* (1983) 44 (8, Sec. 2) and Psychopharmacology (1984) 84:452–456.

Triazolam (8-chloro-6-(2-chlorophenyl)-1-methyl-4H-1,2,4-triazolo-(4,3-a)-1,4-benzodiazepine is a short half-life benzodiazepine drug. It is sold commercially in the U.S. under the brand name Halcion in the form of oral tablets for treatment of insomnia. It is given orally at does of 125–250 µg.

Japanese Pat. Pub. 61254519 describes formulations of drugs with polyvinyl acetate and sulfoxides such as dimethylsulfoxide for transdermal administration. The publication suggests administering benzodiazepines from such formulations but does not mention alprazolam or triazolam. Similarly, Japanese Pat. Pub. 61033129 describes pharmaceutical formulations of various drugs in sesquiterpene alcohol and a polar compound for transdermal administration. It, too, mentions benzodiazepines but says nothing about alprazolam or triazolam.

The present invention is directed to achieving noninvasive sustained administration of short and intermediate half-life benzodiazepines, particularly alprazolam or triazolam, at therapeutically effective levels by delivering them in combination with a skin permeation enhancer transdermally.

DISCLOSURE OF THE INVENTION

Accordingly, one aspect of the invention is a method for providing short or intermediate half-life benzodiazepine therapy to an individual in need of such therapy comprising administering a therapeutically effective amount of said benzodiazepine to the individual transdermally through a predetermined area of skin over a sustained time period at a controlled rate in combination with a sufficient amount of a permeation enhancer to enable the benzodiazepine to permeate the area of skin at a rate in excess of about one $\mu g/cm^2/hr$.

Another aspect of the invention is a laminated composite for administering a short or intermediate half-life benzodiazepine to an individual transdermally through a predetermined area of skin of the individual comprising:

a) a backing layer that is substantially impermeable to the benzodiazepine; and b) a reservoir layer comprising a solvent-based acrylate polymer, the benzodiazepine dissolved in said polymer, and a permeation enhancer that increases the permeability of the skin to the benzodiazepine dissolved in said polymer, the basal surface of said reservoir layer being adapted to be adhered to said area of skin and wherein the amounts of the benzodiazepine and enhancer in said reservoir layer are sufficient to enable a therapeutically effective amount of the benzodiazepine to be administered at a rate in excess of about 1 $\mu g/cm^2/hr$ to the individual through said predetermined area of skin over a sustained time period.

BRIEF DESCRIPTION OF THE DRAWING

The drawing shows an embodiment of a skin patch for administering a short or intermediate half-life benzodiazepine transdermally.

MODES FOR CARRYING OUT THE INVENTION

Figure 1:
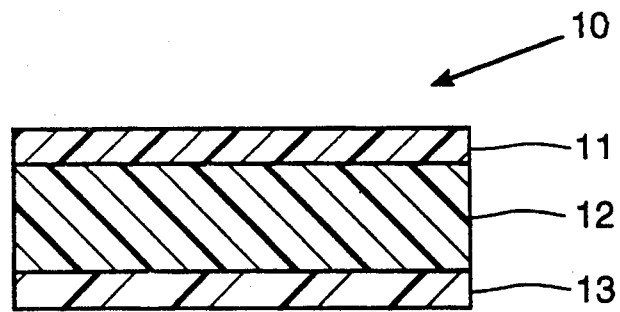

As used herein, the term "transdermal" intends both percutaneous and transmucosal administration, i.e., passage of a short or intermediate half-life benzodiazepine through intact unbroken skin or mucosal tissue into circulation.

As used herein, the term "short and intermediate half-life benzodiazepines" is intended to include those benzodiazepines that have elimination half-life of less than about 24 hrs, preferably less than about 16 hrs. Short and intermediate half-life benzodiazepines include alprazolam, bromazepam, lorazepam, oxazepam, temazepam, and triazolam.

As used herein, the term "benzodiazepine therapy" means those medical conditions for which the particular short- or intermediate-acting benzodiazepine is indicated. For instance, in the case of alprazolam, such therapy includes, without limitation, the treatment of anxiety, depression, panic, or substance (e.g., alcohol, nicotine) withdrawal symptoms. Correspondingly, in the case of triazolam, such therapy includes, without limitation, insomnia.

As used herein, the term "therapeutically effective amount" intends that dose of the benzodiazepine that provides the desired therapy. In the case of alprazolam, the dose is normally in the range of about 0.75 to 6 mg per day and may vary depending upon the patient and the indication being treated. In the case of triazolam, the dose is normally in the range of 0.1 to 1.0 mg/day, more usually 0.25 to 0.50 mg/day.

As used herein, the phrase "sustained time period" means at least about one day and will typically intend a period in the range of about 1 to 3 days in the case of alprazolam and at least about 16 hr, typically 2 to 24 hr, in the case of triazolam.

As used herein, the term "predetermined area of skin" intends a defined area of intact unbroken living skin or mucosal tissue. That area will usually be in the range of about 20 $cm^2$ to about 100 $cm^2$, more usually 20 $cm^2$ to 60 $cm^2$.

As used herein, the term "controlled rate" intends a time course of benzodiazepine administration to circulation that is predetermined and governed by the area of skin through which the drug is passed, the permeability of the skin to the drug, and the activity of the drug maintained in the formulation over the duration of administration.

"Permeation enhancement" as used herein relates to an increase in the permeability of skin to the benzodiazepine as compared to the permeability of skin to the benzodiazepine as measured by the diffusion cell apparatus described in the examples using the benzodiazepine formulated in propylene glycol as a control.

Based on the published pharmacokinetic data on alprazolam, applicants estimated that skin flux in the range of at least about 1 $\mu g/cm^2/hr$ would be required to deliver therapeutically effective amounts of alprazolam transdermally through a practical skin area (i.e., less than about 100 cm$^2$). However, when applicants measured the in vitro flux of alprazolam through skin from a propylene glycol solution, they found the flux was several-fold less than the flux required to deliver a therapeutic amount of the drug through such an area of skin. Applicants thus attempted to enhance the flux of the drug through skin by using various permeation enhancers and found that the skin flux could be increased to levels that make transdermal administration practical with some of those enhancers. This finding enabled applicant to develop formulations and laminated composites that permit short and intermediate half-life benzodiazepines to be administered transdermally through a practical area of skin at rates that result in plasma levels of the benzodiazepine that provide desired therapeutic effects.

A preferred laminated composite for administering alprazolam or triazolam transdermally to humans is shown in the drawing. This composite, generally designated 10, comprises a backing lamina 11, a reservoir lamina 12, and a release liner lamina 13.

The backing layer provides a protective covering for the composite and may itself be a single layer or a multiplicity of layers. For instance, if the composite is to be worn for periods in excess of a day or two, it is desirable to make the backing from an elastomeric polymer such as polyurethane, polyether amide, or copolyester. For devices that are intended to be worn for shorter durations, the backing may be made from relatively flexible but not elastomeric occlusive polymers such as polyester, polyethylene, and polypropylene. The thickness of the backing layer will normally be in the range of about 15 microns to about 250 microns.

The reservoir lamina is preferably composed of the benzodiazepine, a permeation enhancer selected from the group consisting of an ester of the formula $[CH_3(CH_2)_mCOO]_nR$ in which m is an integer from 8 to 16, preferably 8 to 12, most preferably 10; n is 1 or 2, preferably 1; and R is a lower alkyl ($C_1$-$C_3$) residue which may be substituted with 0 to hydroxyl groups, a fatty alcohol of 8 to 16 carbon atoms, fatty acids of 8 to 16 acids, mixed vegetable oil (a mixture of coconut oil and soybean oil in a weight ratio between 9:1 and 1:9), or mixtures thereof, and a solvent-based acrylate polymer adhesive. The drug is present in the layer in excess of its solubility in the two other components. It will normally constitute about 1% to about 10% by weight of the lamina. The enhancer is present in the layer in amounts ranging between about 2 to about 20% by weight. The preferred esters of the above formula are lower alkyl ($C_1$-$C_3$) esters of lauric acid, with propylene glycol monolaurate (PGML) and glyceryl monooleate being particularly preferred. Lauryl alcohol is a preferred fatty alcohol and lauric acid is a preferred fatty acid. It will be appreciated by those skilled in the art that commercially available PGML is normally a mixture of propylene glycol monolaurate, propylene glycol dilaurate and either propylene glycol or methyl laurate or both. Thus "propylene glycol monolaurate" is intended to encompass the pure compound as well as the mixture that is sold commercially. The thickness of the reservoir layer will normally be in the range of 20 microns to 150 microns, preferably 25 microns to 100 microns.

The reservoir lamina plays two functional roles, namely, it is a reservoir for the benzodiazepine and the enhancer, and its adhesive and basal surface provides the means by which the composite is affixed to the skin. The basal release liner lamina 13 is a protective coating for the reservoir lamina during storage and prior to affixation to the skin. This layer is removed from the composite before the composite is affixed to the skin.

The reservoir layer may be formulated by conventional methods known in the field of transdermal drug delivery devices and the three layers assembled into a laminated composite by like methods. These methods and specific embodiments of the invention are further illustrated by the following examples. These examples are not intended to limit the invention in any manner.

EXAMPLE 1

In Vitro Skin Flux of Alprazolam From Various Liquid Formulations

Alprazolam Formulations

Formulations of alprazolam (obtained from Fermion Corp.) in propylene glycol were used. Candidate permeation enhancers (10% w/w) were added to the control formulation of the drug in propylene glycol alone. Excess alprazolam was present.

Skin Permeation Methodology

Human cadaver skin was used for in vitro permeation studies. Frozen skins were thawed and epidermal layers (stratum corneum and viable epidermis) were separated from the full-thickness skin by immersion in water at 60° C. for 2 minutes. This epidermis was either used immediately for diffusion studies or stored at −20° C. for later studies.

The skin sections were mounted carefully between the half cells of a modified Franz cell. The receiver compartment was filled with 10% ethanol, 90% saline solution. The experiment was initiated by placing 500 $\mu l$ test alprazolam formulation in the donor compartment. The Franz cells were placed in an incubator at 32° C. At predetermined times, a 1 ml aliquot was withdrawn from the receiver and replaced with fresh receptor solution. Samples were assayed by HPLC using UV detection at 229 nm. Adequate chromatographic resolution was achieved using a Zorbax Rx C-18 column. The mobile phase was 65% methanol:acetonitrite (1:3) with 35% water containing 0.01% phosphoric acid.

Skin flux ($\mu g/cm^2/hr$) was determined from the steady-state slope of a plot of the cumulative amount of alprazolam permeated through the skin versus time.

RESULTS

The permeation of alprazolam from the test formulations through cadaver skin at 32° C. is presented in Tables 1 and 2 below. (Two sets of tests were made using different skins.)

TABLE 1

| No. | Formulation | Skin Flux (μg/cm²/hr) |
|---|---|---|
| 1. | PG alone (control) | 0.19 (0.22, 0.16) |
| 2. | PG alone(a) | 0.15 (0.13, 0.16) |
| 3. | 10% PGML | 15.80 ± 5.93 |
| 4. | 10% Ethanol | 1.55 (1.33, 1.78) |
| 5. | 10% Transcutol | 0.54 ± 0.10 |
| 6. | 10% Glyceryl Monooleate | 2.80 ± 0.90 |
| 7. | 10% Disodium Sulfosuccinate | 0.62 ± 0 23 |
| 8. | 10% Cocaamido Propyl Betaine | 0.57 ± 0.34 |

(a)Receptor Media = Normal saline alone

TABLE 2

| No. | Formulation | Skin Flux (μg/cm²/hr) |
|---|---|---|
| 1. | PG (control) | 0.34 ± 0.07 |
| 2. | 10% Isopropyl Myristate | 2.92 ± 1.52 |
| 3. | 10% Lauryl Alcohol | 29.92 ± 6.75 |
| 4. | 10% Softigen 767 | 0.67 (0.94, 0.40) |
| 5. | 10% Tetraethylene glycol dimethyl ether | 0.23 ± 0.07 |
| 6. | 10% Mixed Vegetable Oil* | 5.09 ± 0.02 |
| 7. | 10% Lauric Acid, N,N.-dimethylamide | 4.43 (2.16, 6.69) |
| 8. | 10% Neopentyl glycol dicaprate | 1.88 ± 0.21 |

*Coconut-soybean mix, Drewmulse D-4661, Stepan, Maywood, New Jersey

As indicated, significant enhancement of skin flux was achieved only with fatty acid ester, fatty alcohol, fatty acid and mixed vegetable oil enhancers.

EXAMPLE 2

In Vitro Skin Flux of Alprazolam From Laminated Composite

Prototype laminated composites were prepared as follows. Five percent of alprazolam, 15% permeation enhancer, and a solvent-based acrylate polymer (Gelva 788) were mixed thoroughly, using a vortex to obtain homogeneous suspension of the alprazolam in the polymer/enhancer solution. A 75 micron thick film of this mix was cast into a polyester release liner (3M #1022) with a knife. The cast film was dried at 70° C. for 2 hr, die cut to 3 cm², the release liner was removed and the film was placed on the skin section of the diffusion cell. Alprazolam skin flux was measured as in Example 1. The results of these tests are given in Table 3 below.

TABLE 3

| No. | Reservoir Composition | Av. Skin Flux (μg/cm²/hr) |
|---|---|---|
| 1. | 5% alprazolam - Gelva 788 | 0.69 ± 0.01 |
| 2. | 5% alprazolam + 15% PGML - Gelva 788 | 1.36 ± 0.06 |
| 3. | 5% alprazolam + 15% glyceryl monooleate - Gelva 788 | 1.51 ± 0.05 |
| 4. | 5% alprazolam + 15% mixed vegetable oil - Gelva 788 | 1.42 ± 0.07 |
| 5. | 5% alprazolam + 15% glyceryl monooleate - 5% PGML - Gelva 788 | 1.76 ± 0.36 |
| 6. | 5% alprazolam - 15% mixed vegetable oil + 5% PGML - Gelva 788 | 1.69 ± 0.07 |

EXAMPLE 3

In Vitro Skin Flux of Triazolam From Various Liquid Formulations

Triazolam formulations were prepared and tested as in Example 1. The details of these formulations and the results of the tests are shown in Table 4 below.

TABLE 4

| No. | Formulation | Skin Flux (μg/cm²/hr) |
|---|---|---|
| 1. | Triazolam saturated in PG | 0.091 ± 0.031 |
| 2. | Triazolam (saturated) + 10% Lauryl Alcohol in PG | 13.23 ± 8.31 |
| 3. | Triazolam (saturated) + 10% PGML in PG | 8.642 ± 7.52 |
| 4. | Triazolam (saturated) + 10% Glyceryl Monooleate in PG | 1.166 ± 0.63 |
| 5. | Triazolam (saturated) + 10% Mixed Vegetable Oil in PG | 6.71 ± 5.25 |

These data confirm that fatty acid esters, fatty alcohols, and mixed vegetable oils effectively enhance the skin flux of short and intermediate half-life benzodiazepines.

Modifications of the above-described modes for carrying out the invention that are obvious to those of skill in the field of transdermal drug delivery devices are intended to be within the scope of the following claims. For instance, liquid reservoirs of drug could be used in place of the solid state matrices described in the examples.

We claim:

1. A method for providing short or intermediate half-life benzodiazepine therapy to a human patient in need of such therapy comprising administering a therapeutically effective amount of the benzodiazepine to the patient transdermally through a predetermined area of intact skin over a sustained time period at a controlled rate in combination with a sufficient amount of a permeation enhancer to enable the benzodiazepine to permeate the area of intact skin at a rate in excess of about one μg/cm²/hr said benzodiazepine being selected from the group consisting of alprazalam, bromazepam, lorazepam, oxazepam, temazepam and triazolam, and wherein said permeation enhancer is selected from the group consisting of propylyene glycol monolaurate, glyceryl monooleate, lauryl alcohol, mixed vegetable oil or combinations thereof.

2. The method of claim 1 wherein the benzodiazepine is alprazolam and the alprazolam is administered at a rate of about 0.75 to 6 mg/day.

3. The method of claim 1 wherein the benzodiazepine is triazolam and the triazolam is administered at a rate of 0.1 to 1.0 mg/day.

4. The method of claim 1 wherein the benzodiazepine is alprazolam or triazolam and the enhancer is propylene glycol monolaurate, glyceryl monooleate, lauryl alcohol, mixed vegetable oil, or combinations thereof.

5. The method of claim 1 wherein the area of skin is 20 to 60 cm², the benzodiazepine is alprazolam and the alprazolam is administered at a rate of at least about 100 μg/hr.

6. A laminated composite for administering a short or intermediate half-life benzodiazepine to an individual transdermally through a predetermined area of intact skin comprising:

a) a backing layer that is substantially impermeable to the benzodiazepine; and b) a reservoir layer comprising a solvent-based acrylate adhesive polymer, the benzodiazepine dissolved in said polymer, and a permeation enhancer that increases the permeability of the intact skin to the benzodiazepine dissolved in said polymer, the basal surface of said reservoir being adapted to be adhered to said area of intact skin and wherein the amounts of the benzodiazepine and enhancer in said reservoir layer are sufficient to enable a therapeutically effective amount of the benzodiazepine to be administered at a rate in excess of about one $\mu g/cm^2/hr$ to the individual through said predetermined area of intact skin over a sustained time period.

7. The laminated composite of claim 6 wherein the benzodiazepine is alprazolam or triazolam and the permeation enhancer is propylene glycol monolaurate, glyceryl monooleate, lauryl alcohol, mixed vegetable oil, or combinations thereof.

8. The laminated composite of claim 6 wherein the benzodiazepine constitutes 1 to 10% by weight of the reservoir lamina and the permeation enhancer constitutes 2 to 20% by weight of the reservoir lamina.

9. The method of claim 2 wherein the permeation enhancer is a fatty acid ester, a fatty acid, or mixtures thereof.

10. The method of claim 5 wherein the permeation enhancer is a fatty acid ester, a fatty acid, or mixtures thereof.

* * * * *